(12) United States Patent
Karras et al.

(10) Patent No.: US 7,585,968 B2
(45) Date of Patent: Sep. 8, 2009

(54) COMPOSITIONS AND THEIR USES DIRECTED TO THYMUS AND ACTIVATION-REGULATED CHEMOKINE (TARC)

(75) Inventors: James G. Karras, San Marcos, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/390,894

(22) Filed: Mar. 27, 2006

(65) Prior Publication Data
US 2006/0234972 A1    Oct. 19, 2006

Related U.S. Application Data

(60) Provisional application No. 60/666,258, filed on Mar. 28, 2005.

(51) Int. Cl.
*C07H 21/02* (2006.01)
*C07H 21/04* (2006.01)

(52) U.S. Cl. .............. 536/24.5; 536/23.1; 536/24.3; 536/24.33

(58) Field of Classification Search .............. 536/23.1, 536/24.3, 24.33, 24.5; 514/44
See application file for complete search history.

(56) References Cited

U.S. PATENT DOCUMENTS

| | | | |
|---|---|---|---|
| 5,789,573 A | 8/1998 | Baker et al. | |
| 5,801,154 A | 9/1998 | Baracchini et al. | |
| 5,898,031 A | 4/1999 | Crooke | |
| 6,107,094 A | 8/2000 | Crooke | |
| 6,210,892 B1 | 4/2001 | Bennett et al. | |
| 6,426,221 B1 | 7/2002 | Ward et al. | |
| 6,537,775 B1* | 3/2003 | Tournier-Lasserve et al. ............ | 435/69.1 |
| 6,582,908 B2 | 6/2003 | Fodor et al. | |
| 6,617,162 B2 | 9/2003 | Dobie et al. | |
| 6,699,677 B1 | 3/2004 | Schall et al. | |
| 7,250,496 B2* | 7/2007 | Bentwich ............... | 536/23.1 |
| 2002/0049173 A1 | 4/2002 | Bennett et al. | |
| 2003/0228597 A1 | 12/2003 | Cowsert et al. | |
| 2004/0171566 A1 | 9/2004 | Monia et al. | |
| 2004/0235164 A1 | 11/2004 | Bennett et al. | |
| 2004/0266714 A1* | 12/2004 | Freier et al. ............ | 514/44 |

FOREIGN PATENT DOCUMENTS

| | | |
|---|---|---|
| WO | 9835978 A1 | 8/1998 |
| WO | 9960166 A1 | 11/1999 |
| WO | 0240647 A1 | 5/2002 |
| WO | 02088328 A2 | 11/2002 |
| WO | 2004108945 A2 | 12/2004 |

OTHER PUBLICATIONS

Skerra, A. (Nucleic Acids Research, 1992 vol. 20:3551-3554.*

(Continued)

*Primary Examiner*—Sean McGarry
*Assistant Examiner*—Terra Cotta Gibbs (57) ABSTRACT

Disclosed herein are compounds, compositions and methods for modulating the expression of TARC in a cell, tissue or animal. Also provided are methods of target validation. Also provided are uses of disclosed compounds and compositions in the manufacture of a medicament for treatment of diseases and disorders related to expression of TARC, airway hyperresponsiveness, and/or pulmonary inflammation.

30 Claims, 1 Drawing Sheet

OTHER PUBLICATIONS

Agrawal, S. et al., "Antisense therapeutics: is it as simple as complementary base recognition?" Molecular Medicine Today (2000) 6:72-81.

Bonecchi, R. et al., "Differential Expression of Chemokine Receptors and Chemotactic Responsiveness of Type 1 T Helper Cells (TH1s) and TH2s," J. Exp. Med. (1998) 187(1):129-134.

Branch, A. D., "A good antisense molecule is hard to find," TIBS (1998) 23:45-50.

Campbell, J. J. et al., "The chemokine receptor CCR4 in vascular recognition by cutaneous but not intestinal memory T cells," Nature (1999) 400:776-780.

Clemetson, K. J. et al., "Functional expression of CCR1, CCR3, CCR4, and CXCR4 chemokine receptors on human platelets," Blood (2000) 96(13):4046-4054.

Crooke, S. T., "Basic Principles of Antisense Therapeutics," Antisense Research and Application (1998) Springer-Verlag, New York, pp. 1-50.

Gear, A. R. L. et al., "Adenosine diphosphate strongly potentiates the ability of the chemokines MDC, TARC, and SDF-1 to stimulate platelet function," Blood (2001) 97:937-945.

Green, D. W. et al., "Antisense Oligonucleotides: An Evolving Technology for the Modulation of Gene Expression in Human Disease," J. Am. Coll. Surg. (2000) 191:93-105.

Imai, T. et al., "Molecular Cloning of a Novel T Cell-directed CC Chemokine Expressed in Thymus by Signal Sequence Trap Using Epstein-Barr Virus Vector," J. Biol. Chem. (1996) 271(35):21514-21521.

Imai, T. et al., "The T Cell-directed CC Chemokine TARC is a Highly Specific Biological Ligand for CC Chemokine Receptor 4," J. Biol. Chem. (1997) 272(23):15036-15042.

Imai, T. et al., "Selective recruitment of CCR4-bearing Cells toward antigen-presenting cells by the CC chemokines thymus and activation-regulated chemokine and macrophage-derived chemokine," Int. Immunol. (1999) 11(1):81-88.

Jen, K.-Y. et al., "Suppression of Gene Expression by Targeted Disruption of Messenger RNA: Available Options and Current Strategies," Stem Cells (2000) 18:307-319.

Kawasaki, S. et al., "Intervention of Thymus and Activation-Regulated Chemokine Attenuates the Development of Allergic Airway Inflammation and Hyperresponsiveness in Mice," J. Immunol. (2001) 166:2055-2062.

Kumar, R. K. et al., "Murine Model of Chronic Human Asthma," Immunology and Cell Biology (2001) 79:141-144.

Nyce, J. W., "Respirable antisense oligonucleotides as novel therapeutic agents for asthma and other pulmonary diseases," Expert. Opin. Invest. Drugs (1997) 6(9):1149-1156.

Nyce, J. W. et al., "DNA antisense therapy for asthma in an animal model," Nature (1997) 385(6618):721-725.

Richards, I. M., "Mouse models of allergic disease; how do they related to asthma in man?" Clinical and Experimental Allergy (1996) 26:618-620.

Sallusto, F. et al., "Distinct patterns and kinetics of chemokine production regulate dendritic cell function," Eur. J. Immunol. (1999) 29:1617-1625.

Sallusto, F. et al., "Flexible Programs of Chemokine Receptor Expression on Human Polarized T Helper 1 and 2 Lymphocytes," J. Exp. Med. (1998) 187(6):875-883.

Sekiya, T. et al., "Inducible Expression of a Th2-Type CC Chemokine Thymus- and Activation-Regulated Chemokine by Human Bronchial Epithelial Cells," J. Immunol. (2000) 165:2005-2213.

Temelkovski, J. et al., "An improved murine model of asthma selective airway inflammation, epithelial lesions and increased methacholine responsiveness following chronic exposure to aerosolised allergan," Thorax (1998) 53:849-856.

Terada, N. et al., "Expression of C-C chemokine TARC in human nasal mucosa and its regulation by cytokines," Clin. Exp. Allergy (2001) 31:1923-1931.

Berin, "The Role of TARC in the Pathogenesis of Allergic Asthma" Drug News Perspect (2002) 15:10-16.

Chin, "On the preparation and Utilization of Isolated and Purified Oligonucleotides" Document purportedly located on a CD-Rom and contributed to the public collection of the Katherine R. Everett Law Library of the University of North Carolina on Mar. 14, 2002.

Humbert et al., "The immunopathology of extrinsic (atopic) and intrinsic (non-atopic) asthma: more similarities than differences" Immunology Today (1999) 20: 528-533.

International Search Report for Application No. PCT/US06/11478 dated Nov. 6, 2006 (BIOL0080W0).

Kakinuma et al., "Thymus and activation-regulated chemokine in atopic dermatitis: Serum thymus and activation-regulated chemokine level is closely related with disease activity" J Allergy Clin Immunol (2001) 107: 535-541.

Katoh et al., "Accumulation of CCR4-expressing CD4+T cells and high concentration of its ligands (TARC and MDC) in bronchoalveolar lavage fluid of patients with eosinophilic pneumonia" Allergy (2003) 58:518-523.

New England Biolabs 1998/1999 Catalog, cover page, pp. 121 and 284.

Nomiyama et al., "Assignment of the human CC chemokine gene TARC (SCYA17) to chromosme 16q13" Genomics (1997) 40: 211-213.

Nomiyama et al., "Human chemokines fractalkine (SCYD1), MDC (SCYA22) and Tarc (SCYA17) are clustered on chromsome 16q13" Cytogenet Cell Genet (1998) 81: 10-11.

Reynolds et al., "Rational siRNA design for RNA interference" Nature Biotechnology (2004)22(3): 326- 330.

Tijsterman et al., "RNA helicase MUT-14-dependent gene silencing triggered by C. elegant by short antisense RNAs" Science (2002) 295:694-697.

Vestergaard et al., "Overproduction of TH2-specific chemokines in NC/Nga mice exhibiting atopic dermatitis-like lesions" J Clin Invest (1999) 104:1097-1105.

Vestergaard et al., "A Th2 chemokine, TARC, produced by keratinocytes may recruit CLA+CCR4+ lymphocytes into lesional atopic dermatitis skin" J. Invest Dermatol, (2000) 115: 640-646.

Vickers et al., "Efficient reduction of target RNAs by small interfering RNA and Rnase H-dependent antisense agents. A comparative analysis" J. Biol. Chem (2003) 278: 7108-7118.

* cited by examiner

COMPOSITIONS AND THEIR USES DIRECTED TO THYMUS AND ACTIVATION-REGULATED CHEMOKINE (TARC)

CROSS-REFERENCE TO RELATED APPLICATIONS

This application claims priority to U.S. Provisional Patent Application Ser. No. 60/666,258, filed Mar. 28, 2005 which is incorporated herein by reference in its entirety.

INCORPORATION OF SEQUENCE LISTING

A copy of the sequence listing in both a paper and a computer-readable form is provided herewith and hereby incorporated by reference. The computer readable form is provided on 3.5" diskette containing the file named BIOL0080USSEQ.txt

BACKGROUND OF THE INVENTION

Allergic rhinitis and asthma are widespread conditions with complex and multifactorial etiologies. The severity of the conditions vary widely between individuals, and within individuals, dependent on factors such as genetics, environmental conditions, and cumulative respiratory pathology associated with duration and severity of disease. Both diseases are a result of immune system hyperresponsiveness to innocuous environmental antigens, with asthma typically including an atopic (i.e., allergic) component.

In asthma, the pathology manifests as inflammation, mucus overproduction, and reversible airway obstruction which may result in scarring and remodeling of the airways. Mild asthma is relatively well controlled with current therapeutic interventions including beta-agonists and low dose inhaled corticosteroids or cromolyn. However, moderate and severe asthma are less well controlled, and require daily treatment with more than one long-term control medication to achieve consistent control of asthma symptoms and normal lung function. With moderate asthma, doses of inhaled corticosteroids are increased relative to those given to mild asthmatics, and/or supplemented with long acting beta-agonists (LABA) (e.g., salmeterol) or leukotriene inhibitors (e.g., montelukast, zafirlukast). Although LABA can decrease dependence on corticosteroids, they are not as effective for total asthma control as corticosteroids (e.g., reduction of episodes, emergency room visits) (Lazarus et al., JAMA. 2001.285: 2583-2593; Lemanske et al., JAMA. 2001. 285: 2594-2603). With severe asthma, doses of inhaled corticosteroids are increased, and supplemented with both LABA and oral corticosteroids. Severe asthmatics often suffer from chronic symptoms, including night time symptoms; limitations on activities; and the need for emergency room visits. Additionally, chronic corticosteroid therapy at any level has a number of unwanted side effects, especially in children (e.g., damage to bones resulting in decreased growth).

Allergic rhinitis is inflammation of the nasal passages, and is typically associated with watery nasal discharge, sneezing, congestion and itching of the nose and eyes. It is frequently caused by exposure to irritants, particularly allergens. Allergic rhinitis affects about 20% of the American population and ranks as one of the most common illnesses in the US. Most suffer from seasonal symptoms due to exposure to allergens, such as pollen, that are produced during the natural plant growth season(s). A smaller proportion of sufferers have chronic allergies due to allergens that are produced throughout the year such as house dust mites or animal dander. A number of over the counter treatments are available for the treatment of allergic rhinitis including oral and nasal antihistamines, and decongestants. Antihistamines are utilized to block itching and sneezing and many of these drugs are associated with side effects such as sedation and performance impairment at high doses. Decongestants frequently cause insomnia, tremor, tachycardia, and hypertension. Nasal formulations, when taken improperly or terminated rapidly, can cause rebound congestion. Anticholinergics and montelukast have substantially fewer side effects, but they also have limited efficacy. Similarly, prescription medications are not free of side effects. Nasal corticosteroids can be used for prophylaxis or suppression of symptoms; however, compliance is variable due to side effects including poor taste and nasal irritation and bleeding. Allergen immunotherapy is expensive and time consuming and carries a low risk of anaphylaxis.

Persistent nasal inflammation can result in the development of nasal polyps. Nasal polyps are present in about 4.2% of patients with chronic rhinitis and asthma (4.4% of men and 3.8% of women) (Grigores et al., Allergy Asthma Proc. 2002, 23:169-174). The presence of polyps is increased with age in both sexes and in patients with cystic fibrosis and aspirin-hypersensitivity triad. Nasal polyposis results from chronic inflammation of the nasal and sinus mucous membranes. Chronic inflammation causes a reactive hyperplasia of the intranasal mucosal membrane, which results in the formation of polyps. The precise mechanism of polyp formation is incompletely understood. Nasal polyps are associated with nasal airway obstruction, postnasal drainage, dull headaches, snoring, anosmia, and rhinorrhea. Medical therapies include treatment for underlying chronic allergic rhinitis using antihistamines and topical nasal steroid sprays. For severe nasal polyposis causing severe nasal obstruction, treatment with short-term steroids may be beneficial. Topical use of cromolyn spray has also been found to be helpful to some patients in reducing the severity and size of the nasal polyps. Oral corticosteroids are the most effective medication for the short-term treatment of nasal polyps, and oral corticosteroids have the best effectiveness in shrinking inflammatory polyps. Intranasal steroid sprays may reduce or retard the growth of small nasal polyps, but they are relatively ineffective in massive nasal polyposis. Although nasal polyps can be treated pharmacologically, many of the therapeutics have undesirable side effects. Moreover, polyps tend to be recurrent, eventually requiring surgical intervention. Compositions and methods to inhibit post-surgical recurrence of nasal polyps are not presently available.

Other diseases characterized by similar inflammatory pathways include, but are not limited to, chronic bronchitis, pulmonary fibrosis, emphysema, chronic obstructive pulmonary disease (COPD), eosinophilic pneumonia, and pediatric asthma.

Thymus and Activation-Related Chemokine (TARC) and Inflammatory Signaling Pathways It is generally acknowledged that allergy and asthma are a result of the dysregulation of T cell-mediated immunity resulting in a bias towards a Th2 response (enhanced production of interleukin-4 (IL-4) IL-5 and IL-13). The presence of CD4+ T cells producing IL-4, IL-5 and IL-13 cytokines in bronchoalveolar lavage fluid and in airway epithelial biopsies of asthmatics has been clearly documented. TARC, a selective chemoattractant for Th2 cells produced by the lung epithelium and dendritic cells, has been shown to be present at higher levels in the lungs of asthmatics as compared to normal subjects (Sekiya et al., J. Immunol. 2000. 165:2205-2213). IL 4 and TNF-α have been shown to promote production of TARC in the bronchial epithelial A549 cell line.

Evidence for an in vivo role of TARC in allergic inflammation derives from a study showing that pretreatment of sensitized mice with an anti-TARC antibody prevents airway eosinophilia in an allergic asthma model, with a concomitant decrease of both infiltrating lymphocytes and levels of certain inflammatory cytokines, including IL-4 and IL-13 (Kawasaki et al., Journal of Immunology, 2001, 166, 2055-2062). More recently, it has been shown that asthmatic patients exposed to a relevant allergen release large quantities of TARC in bronchoalveolar fluid, as do patients with eosinophilic pneumonia. (Berin, Drug News Perspect, 2002, 15, 10-16; Katoh et al., Allergy, 2003, 58, 518-523). These observations make components of the Th2 cytokine pathway, including TARC, potential targets for therapeutic intervention for asthma, allergy, and other forms of pulmonary inflammation and/or airway hyperresponsiveness.

Allergic rhinitis is also characterized by infiltration of eosinophils, mast cells, and lymphocytes into the nasal mucosa. Terada et al. (Terada et al., Clin Exp Allergy, 2001, 31, 1923-1931) showed that nasal epithelial cells (NAECs) derived from allergic individuals release higher concentrations of TARC than those derived from normal subjects. Immunohistochemical analysis of nasal biopsies demonstrated that TARC immunoreactivity is mainly localized to the nasal airway epithelium, and to a lesser extent to mononuclear cells in the nasal submucosa.

Imai et al. (J. Biol. Chem., 1996, 271, 21514-21521) first described the isolation and molecular characterization of TARC as a novel CC chemokine from a peripheral blood mononuclear cell (PBMC) cDNA library. TARC is located on chromosome region 16q, is 2176 base pairs in length, and encodes a highly basic preprotein of 94 amino acid residues. After post-translational processing, the mature protein is a 71 amino acid residues polypeptide. TARC is constitutively present in thymus, and upon activation is produced by a number of cellular sources, including PBMCs, monocytes, macrophages, thymic cells, dendritic cells, endothelial cells, and human bronchial cells (Imai et al., J Biol Chem, 1996, 271, 21514-21521; Sallusto et al., Eur J Immunol, 1999, 29, 1617-1625; Campbell et al., Nature, 1999, 400, 776-780; Sekiya et al., J Immunol, 2000, 165, 2205-2213).

TARC induces chemotaxis in certain human T cell lines, but is not chemotactic for either monocytes or granulocytes (Imai et al., J Biol Chem, 1996, 271, 21514-21521; Imai et al., J Biol Chem, 1997, 272, 15036-15042). In vitro studies have shown that TARC induces selective migration of lymphocytes (Imai et al., Int Immunol, 1999, 11, 81-88; Imai et al., J Biol Chem, 1997, 272, 15036-15042; Sallusto et al., J Exp Med, 1998, 187, 875-883; Bonecchi et al., J Exp Med, 1998, 187, 129-134). In addition, TARC induces integrin-dependent adhesion to the intercellular adhesion molecule 1 (ICAM-1) of skin memory T cells subset causing a rapid arrest of such cells under physiological flow conditions (Campbell et al., Nature, 1999, 400, 776-780). TARC has also been found to activate platelets; the effects of TARC on these cells include shape change, adhesion to collagen or fibrinogen, aggregation, and calcium influx (Gear et al., Blood, 2001, 97, 937-945; Clemetson et al., Blood, 2000, 96, 4046-4054).

Antisense Oligonucleotides and Pulmonary Disease

Antisense oligonucleotides (ASOs) are being pursued as therapeutics for pulmonary inflammation, airway hyperresponsiveness, and/or asthma. Lung provides an ideal tissue for aerosolized ASOs for several reasons (Nyce and Metzger, Nature, 1997: 385:721-725, incorporated herein by reference in its entirety); the lung can be targeted non-invasively and specifically, it has a large absorption surface; and is lined with surfactant that may facilitate distribution and uptake of ASOs. Delivery of ASOs to the lung by aerosol results in excellent distribution throughout the lung in both mice and primates. Immunohistochemical staining of inhaled ASOs in normalized and inflamed mouse lung tissue shows heavy staining in alveolar macrophages, eosinophils, and epithelium, moderate staining in blood vessels endothelium, and weak staining in bronchiolar epithelium. ASO-mediated target reduction is observed in dendritic cells, macrophages, eosinophils, and epithelial cells after aerosol administration. The estimated half life of a 2'-methoxyethoxy (2'-MOE) modified oligonucleotide delivered by aerosol administration to mouse or monkey is about 4 to 7, or at least 7 days, respectively. Moreover, ASOs have relatively predictable toxicities and pharmacokinetics based on backbone and nucleotide chemistry. Pulmonary administration of ASOs results in minimal systemic exposure, potentially increasing the safety of such compounds as compared to other classes of drugs.

Compositions and methods for formulation of ASOs and devices for delivery to the lung and nose are well known. ASOs are soluble in aqueous solution and may be delivered using standard nebulizer devices (Nyce, Exp. Opin. Invest. Drugs, 1997, 6:1149-1156). Formulations and methods for modulating the size of droplets using nebulizer devices to target specific portions of the respiratory tract and lungs are well known to those skilled in the art. Oligonucleotides can be delivered using other devices such as dry powder inhalers or metered dose inhalers which can provide improved patient convenience as compared to nebulizer devices, resulting in greater patient compliance.

Generally, the principle behind antisense technology is that an antisense compound hybridizes to a target nucleic acid and effects the modulation of gene expression activity, or function, such as transcription or translation. The modulation of gene expression can be achieved by, for example, target RNA degradation or occupancy-based inhibition. An example of modulation of target RNA function by degradation is RNase H-based degradation of the target RNA upon hybridization with a DNA-like antisense compound. Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. This sequence-specificity makes antisense compounds extremely attractive as tools for target validation and analysis of gene function, as well as therapeutics to selectively modulate the expression of genes involved in diseases.

Antisense oligonucleotides targeted to a number of targets including, but not limited to p38 alpha MAP kinase (U.S. Patent Publication No. 20040171566, incorporated by reference); the CD28 receptor ligands B7.1 and B7.2 (U.S. Patent Publication 20040235164, incorporated by reference); intracellular adhesion molecule (ICAM) (WO 2004/108945, incorporated by reference); and adenosine $A_1$ receptor (Nyce and Metzger, Nature, 1997, 385:721-725) have been tested for their ability to inhibit pulmonary inflammation and airway hyperresponsiveness in mouse, rabbit, and/or monkey models of asthma when delivered by inhalation. Various endpoints were analyzed in each case and a portion of the results are presented herein. ASOs targeted to p38 alpha MAP kinase reduced eosinophil recruitment, airway hyperresponsiveness (AHR), and mucus production in two different mouse models. ASOs targeted to each B7.1 and B7.2 decreased target expression and eosinophil recruitment. An ASO targeted to B7.2 also reduced AHR. ASOs targeted to ICAM-1 decreased AHR and decreased neutrophil and eosinophil recruitment in mice. Treatment of Cynomolgus monkeys with an ASO targeted to ICAM-1 significantly reduced airway impedance (resistance) induced by methacholine challenge in naturally Ascaris allergen-sensitized monkeys. An ASO targeted to adenosine $A_1$ receptor reduced receptor density on airway smooth muscle and reduced AHR in an allergic rabbit model. These data demonstrate that oligonucleotides are effectively delivered by inhalation to cells within the lungs of multiple species, including a non-human primate, and are effective at reducing airway hyperresponsiveness and/or pulmonary inflammation as determined by a number of endpoints.

However, treatment with any ASO targeted to any inflammatory mediator involved in pulmonary inflammation is not always effective at reducing AHR and/or pulmonary inflammation. ASOs targeted to Jun N-terminal Kinase (JNK-1) found to decrease target expression in vitro were tested in a mouse model of asthma. Treatment with each of two different antisense oligonucleotides targeted to JNK-1 were not effective at reducing methacholine induced AHR, eosinophil recruitment, or mucus production at any of the ASO doses tested.

A number of ASOs designed to target TARC have been reported for use as research tools. The PCT publication WO02088328 (Belardelli et al., 2002) discloses the use of an oligonucleotide of 24 nucleotides in length that is complementary to a nucleic acid molecule encoding TARC. U.S. Pat. No. 6,699,677 (Schall et al., 2004) discloses the use of an oligonucleotide of 30 nucleotides in length as a PCR primer for amplifying a nucleic acid molecule encoding TARC. The PCT publication WO0240647 (Ulrich and Saikh, 2002) discloses the use of an oligonucleotide of 30 nucleotides in length as a PCR primer for amplifying a nucleic acid molecule encoding TARC.

The role of TARC in the Th2 inflammatory signaling pathways makes it an attractive therapeutic candidate, as this pathway has been linked to asthma, allergy, and other inflammatory disorders. Currently, there are no known therapeutic agents that effectively inhibit the synthesis of TARC, and all investigative strategies to date aimed at modulating function have involved the use of antibodies. Consequently, there remains a need for additional agents capable of effectively inhibiting the activity of TARC.

SUMMARY OF THE INVENTION

The invention provides compounds, particularly antisense compounds, especially nucleic acid and nucleic acid-like oligomers, which are targeted to a nucleic acid encoding TARC. Preferably, the antisense compounds are antisense oligonucleotides targeted to TARC, particularly human TARC (GenBank Accession No. NM_002987.2, entered Aug. 29, 2002 (SEQ ID NO: 1); and nucleotides (nt) 1658992 to 6171087 of GenBank Accession No. NT_010498.14, entered Feb. 19, 2004), that modulate the expression of TARC. The compounds comprise at least a 12 nucleobase portion, preferably at least a 15 nucleobase portion, of an active target segment, or are at least 80% identical to at least a 15 nucleobase portion an active target segments.

The invention provides a method for modulating the expression of TARC in cells or tissues comprising contacting the cells with at least one compound of the instant invention, and analyzing the cells for indicators of a decrease in expression of TARC mRNA and/or protein by direct measurement of mRNA and/or protein levels, and/or indicators of pulmonary inflammation and/or airway hyperresponsiveness.

The invention further provides a method for the prevention, amelioration, and/or treatment of pulmonary inflammation and/or airway hyperresponsiveness comprising administering at least one compound of the instant invention to an individual in need of such intervention. The compound is preferably administered by aerosol (i.e., topically) to at least a portion of the respiratory tract. The portion of the respiratory tract selected is dependent upon the location of the inflammation. For example, in the case of asthma, the compound is preferably delivered predominantly to the lung. In the case of allergic rhinitis, the compound is preferably delivered predominantly to the nasal cavity and/or sinus. The compound is delivered using any of a number of standard delivery devices and methods well known to those skilled in the art, including, but not limited to nebulizers, nasal and pulmonary inhalers, dry powder inhalers, and metered dose inhalers.

The invention also provides a method of use of the compositions of the instant invention for the preparation of a medicament for the prevention, amelioration, and/or treatment disease, especially a disease associated with and including at least one indicator of pulmonary inflammation and/or airway hyperresponsiveness. The medicament is preferably formulated for aerosol administration to at least a portion of the respiratory tract.

BRIEF DESCRIPTION OF THE DRAWINGS

FIG. 1A shows the acute model of induced allergic inflammation, a prophylaxis treatment paradigm;

FIG. 1B shows the rechallenge model of induced allergic inflammation which allows testing of a pharmacologic approach in mice that have been previously sensitized and then exposed to an aeroallergen; and FIG. 1C shows the chronic model of induced allergic inflammation which uses a therapeutic treatment regimen, with ASO treatment initiated after the establishment local pulmonary inflammation.

DETAILED DESCRIPTION OF THE INVENTION

Asthma, allergy, and a number of other diseases or conditions related to pulmonary inflammation and/or AHR share common inflammatory mediators, including TARC, a Th2 cytokine. Therapeutic interventions for these diseases or conditions are not completely satisfactory due to lack of efficacy and/or unwanted side effects of the compounds. The instant invention provides antisense compounds, preferably antisense compounds, for the prevention, amelioration, and/or treatment of pulmonary inflammation and/or airway hyperresponsiveness. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures which are known to those skilled in the art. As used herein, "treatment" means to administer a composition of the invention to effect an alteration or improvement of the disease or condition. Prevention, amelioration, and/or treatment may require administration of multiple doses at regular intervals, or prior to exposure to an agent (e.g., an allergen) to alter the course of the condition or disease. Moreover, a single agent may be used in a single individual for each prevention, amelioration, and treatment of a condition or disease, sequentially or concurrently. In a preferred method of the instant invention, the ASOs are delivered by aerosol for topical delivery to the respiratory tract, thereby limiting systemic exposure and reducing potential side effects.

Overview

Disclosed herein are antisense compounds, including antisense oligonucleotides and other antisense compounds for use in modulating the expression of nucleic acid molecules encoding TARC. This is accomplished by providing antisense compounds that hybridize with one or more target nucleic acid molecules encoding TARC. As used herein, the terms "target nucleic acid" and "nucleic acid molecule encoding TARC" have been used for convenience to encompass RNA (including pre-mRNA and mRNA or portions thereof) transcribed from DNA encoding TARC, and also cDNA derived from such RNA. In a preferred embodiment, the target nucleic acid is an mRNA encoding TARC.

The principle behind antisense technology is that an antisense compound hybridizes to a target nucleic acid to modulate gene expression activities such as transcription or translation. This sequence specificity makes antisense compounds extremely attractive for therapeutics to selectively modulate the expression of genes involved in disease, as well as tools for target validation and gene functional analysis. Although not limited by mechanism of action, the compounds of the instant invention are proposed to work by an antisense, non-autocatalytic mechanism.

Target Nucleic Acids

"Targeting" an antisense compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes TARC.

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Antisense compounds targeted to such variants are within the scope of the instant invention.

Target Names, Synonyms, Features

In accordance with the present invention are compositions and methods for modulating the expression of TARC (also known as A-152E5.3; ABCD-2; CCL17; SCYA17; small inducible cytokine A17 precursor; T cell-directed CC chemoline; Thymus- and Activation-regulated Chemokine; chemokine (C-C motif) ligand 17; thymus and activation-regulated chemokine; and small inducible cytokine subfamily A (Cys-Cys), member 17). Table 1 lists the GenBank accession numbers of sequences corresponding to nucleic acid molecules encoding TARC (nt=nucleotide), the date the version of the sequence was entered in GenBank, and the corresponding SEQ ID NO in the instant application, when assigned, each of which is incorporated herein by reference.

TABLE 1

Gene Targets

| Species | Genbank # | Genbank Date | SEQ ID NO |
|---------|-----------|--------------|-----------|
| Human | NM_002987.2 | 29 Aug. 2002 | 1 |
| Human | NT_010498.14, nt 6158992 to 6171087 | 19 Feb. 2004 | |
| Mouse | AF125570.1 | 28 Sep. 1999 | 3 |
| Mouse | AF125571.1 | 28 Sep. 1999 | |
| Mouse | AF125572.1 | 28 Sep. 1999 | |
| Mouse | AF192527.2 | 03 Nov. 1999 | |
| Mouse | AJ242587.1 | 15 Apr. 2005 | |
| Mouse | NT_078586.1, nt 3342292 to 3344858 | 30 Oct. 2003 | |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of TARC. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of antisense compounds of the present invention on target nucleic acid expression can be tested in any of a variety of cell types provided that the target nucleic acid is present at measurable levels. The effect of antisense compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and other public sources, and are well known to those skilled in the art. Primary cells, or those cells which are isolated from an animal and not subjected to continuous culture, can be prepared according to methods known in the art, or obtained from various commercial suppliers. Additionally, primary cells include those obtained from donor human subjects in a clinical setting (i.e. blood donors, surgical patients). Primary cells prepared by methods known in the art.

Assaying Modulation of Expression

Modulation of TARC expression can be assayed in a variety of ways known in the art. TARC mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by TARC can be quantitated in a variety of ways well known in the art, such as immunoprecipitation, Western blot analysis (immunoblotting), ELISA or fluorescence-activated cell sorting (FACS). Antibodies directed to a protein encoded by TARC can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997.

Active Target Segments

The locations on the target nucleic acid defined by having one or more active antisense compounds targeted thereto are referred to as "active target segments." When an active target segment is defined by multiple antisense compounds, the compounds are preferably separated by no more than about 10 nucleotides on the target sequence, more preferably no more than about 5 nucleotides on the target sequence, even more preferably the compounds are contiguous, most preferably the compounds are overlapping. There may be substantial variation in activity (e.g., as defined by percent inhibition) of the antisense compounds within an active target segment. Active antisense compounds are those that modulate the expression of their target RNA. Active antisense compounds inhibit expression of their target RNA at least 10%, preferably 20%. In a preferred embodiment, at least about 50%, preferably about 70% of the oligonucleotides targeted to the active target segment modulate expression of their target RNA at least 40%. In a more preferred embodiment, the level of inhibition required to define an active antisense compound is defined based on the results from the screen used to define the active target segments.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural base 5-methyl cytosine and the artificial base known as a G-clamp. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

Complementarity

"Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most prefereably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA in an oocyte injection model. ASOs 25 nucleobases in length with 8 or 11 mismatch bases near the ends of the ASOs were able to direct specific cleavage of the target MRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358,1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs.

Therapeutics

Antisense compounds of the invention can be used to modulate the expression of TARC in an animal, such as a human. In one non-limiting embodiment, the methods comprise the step of administering to said animal in need of therapy for a disease or condition associated with TARC an effective amount of an antisense compound that inhibits expression of TARC. A disease or condition associated with TARC includes, but is not limited to, pulmonary inflammation and airway hyperresponsiveness. In one embodiment, the antisense compounds of the present invention effectively inhibit the levels or function of TARC RNA. Because reduction in TARC mRNA levels can lead to alteration in TARC protein products of expression as well, such resultant alterations can also be measured. Antisense compounds of the present invention that effectively inhibit the level or function of TARC RNA or protein products of expression are considered an active antisense compounds. In one embodiment, the antisense compounds of the invention inhibit the expression of TARC causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of TARC can be measured in a bodily fluid, tissue or organ of the animal. Methods of obtaining samples for analysis, such as body fluids (e.g., sputum), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of inflammation.

The antisense compounds of the present invention can be utilized in pharmaceutical compositions by adding an effective amount of a compound to a suitable pharmaceutically acceptable diluent or carrier. Acceptable carriers and dilutents are well known to those skilled in the art. Selection of a diluent or carrier is based on a number of factors, including, but not limited to, the solubility of the compound and the route of administration. Such considerations are well understood by those skilled in the art. In one aspect, the compounds of the present invention inhibit the expression of TARC. The compounds of the invention can also be used in the manufacture of a medicament for the treatment of diseases and disorders related to TARC expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of TARC expression in the cells of bodily fluids, organs or tissues. An effective amount can be determined by monitoring the modulatory effect of the antisense compound or compounds or compositions on target nucleic acids or their products by methods routine to the skilled artisan.

Thus, provided herein is the use of an isolated single- or double-stranded antisense compound targeted to TARC in the manufacture of a medicament for the treatment of a disease or disorder by means of the method described above. In a preferred embodiment, the antisense compound is a single stranded antisense compound.

Kits, Research Reagents, and Diagnostics

The antisense compounds of the present invention can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the antisense compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Compounds

The term "oligomeric compound" refers to a polymeric structure capable of hybridizing to a region of a nucleic acid molecule. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides.

An "antisense compound" or "antisense oligomeric compound" refers to an oligomeric compound that is at least partially complementary to the region of a target nucleic acid molecule to which it hybridizes and which modulates (increases or decreases) its expression. This term includes oligonucleotides, oligonucleosides, oligonucleotide analogs, oligonucleotide mimetics, antisense compounds, antisense oligomeric compounds, and chimeric combinations of these. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, the antisense compound comprises a single stranded oligonucleotide. In some embodiments of the invention the antisense compound contains chemical modifications. In a preferred embodiment, the antisense compound is a single stranded, chimeric oligonucleotide wherein the modifications of sugars, bases, and internucleoside linkages are independently selected.

The antisense compounds in accordance with this invention may comprise an antisense compound from about 12 to about 35 nucleobases (i.e. from about 12 to about 35 linked nucleosides). In other words, a single-stranded compound of the invention comprises from about 12 to about 35 nucleobases, and a double-stranded antisense compound of the invention (such as a siRNA, for example) comprises two strands, each of which is independently from about 12 to about 35 nucleobases. This includes oligonucleotides 15 to 35 and 16 to 35 nucleobases in length. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases.

Antisense compounds about 12 to 35 nucleobases in length, preferably about 15 to 35 nucleobases in length, comprising a stretch of at least eight (8), preferably at least 12, more preferably at least 15 consecutive nucleobases selected from within the active target regions are considered to be suitable antisense compounds as well.

Modifications can be made to the antisense compounds of the instant invention and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclice nucleobase analogs such as locked nucleic acids (LNA) and ENA.

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang Each strand of the siRNA duplex may be from about 12 to about 35 nucleobases. In a preferred embodiment, each strand of the siRNA duplex is about 17 to about 25 nucleobases. The two strands may be fully complementary (i.e., form a blunt ended compound), or include a 5' or 3' overhang on one or both strands. Double-stranded compounds can be made to include chemical modifications as discussed herein.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine or a 5-methyl cytosine, whereas a nucleobase mimetic would include more complicated structures, such as for example a tricyclic phenoxazine nucleobase mimetic. Methods for preparation of the above noted modified nucleobases are well known to those skilled in the art.

Antisense compounds of the present invention may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-($CH_2$)$_2$—O-2' bridge); and substituted sugars, especially 2'-sustituted sugars having a 2'-F, 2'-$OCH_2$ or a 2'-O($CH_2$)$_2$—$OCH_3$ substituent group. Sugars can also be replaced with sugar mimetic groups among others. Methods for the preparations of modified sugars are well known to those skilled in the art.

The present invention includes internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)2-O—); and N,N'-dimethylhydrazine (—$CH_2$—N($CH_3$)—N($CH_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this invention, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present invention provides compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds of the instant invention are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound of the present invention.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used in the present invention the term "motif" refers to the orientation of modified sugar moieties and/or sugar mimetic groups in an antisense compound relative to like or differentially modified or unmodified nucleosides. As used in the present invention, the terms "sugars", "sugar moieties" and "sugar mimetic groups" are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an antisense compound.

As used in the present invention the term "gapped motif" refers to an antisense compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The nucleosides located in the gap of a gapped antisense compound have sugar moieties that are different than the modified sugar moieties in each of the wings.

As used in the present invention the term "alternating motif" refers to an antisense compound comprising a contiguous sequence of nucleosides comprising two differentially sugar modified nucleosides that alternate for essentially the entire sequence of the antisense compound, or for essentially the entire sequence of a region of an antisense compound.

As used in the present invention the term "fully modified motif" refers to an antisense compound comprising a contiguous sequence of nucleosides wherein essentially each nucleoside is a sugar modified nucleoside having uniform modification.

As used in the present invention the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified antisense compound.

As used in the present invention the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. Methods of preparation of chimeric oligonucleotide compounds are well known to those skilled in the art.

As used in the present invention the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present invention is meant to include all such possible isomers, as well as their racemic and optically pure forms.

In one aspect of the present invention antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Salts, Prodrugs and Bioequivalents

The antisense compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., phosphodiester backbone linkages) to produce the active compound.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds of the invention may also be admixed, encapsulated, conjugated or otherwise associated with other molecules, molecule structures or mixtures of compounds.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. In a preferred embodiment, administration is topical to the surface of the respiratory tract, particularly pulmonary, e.g., by nebulization, inhalation, or insufflation of powders or aerosols, by mouth and/or nose.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations of the instant invention are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations of the instant invention may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions of the invention can contain two or more antisense compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially. Compositions of the instant invention can also be combined with other non-antisense compound therapeutic agents.

Nonlimiting Disclosure and Incorporation by Reference

While certain compounds, compositions and methods of the present invention have been described with specificity in accordance with certain embodiments, the following examples serve only to illustrate the compounds of the invention and are not intended to limit the same. Each of the references, GenBank accession numbers, and the like recited in the present application is incorporated herein by reference in its entirety.

EXAMPLE 1

Transfection Methods

Cell Types

The effect of antisense compounds on target nucleic acid expression was tested in the following cell types.

A549:

The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in antisense compound transfection experiments.

3T3-L1:

3T3-L1, undifferentiated: The mouse embryonic adipocyte-like cell line 3T3-L1 was obtained from the American Type Culture Collection (Manassas, Va.). 3T3-L1 cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 80% confluence. Cells were seeded into 96-well plates (Falcon-Primaria #3872) at a density of approximately 4000 cells/well for use in antisense compound transfection experiments.

Treatment with Antisense Compounds

When cells reach appropriate confluency, they are treated with oligonucleotide using a transfection lipid and method, such as Lipofectin™ essentially by the manufacturer's instructions, as described.

Briefly, when cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Other transfection reagents and methods (e.g., electroporation) for delivery of oligonucleotides to the cell are well known. The method of delivery of oligonucleotide to the cells is not a limitation of the instant invention.

Control Oligonucleotides

Control oligonucleotides are used to determine the optimal antisense compound concentration for a particular cell line. Furthermore, when antisense compounds of the invention are tested in antisense compound screening experiments or phenotypic assays, control oligonucleotides are tested in parallel with compounds of the invention.

The concentration of oligonucleotide used varies from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 µM to 40 µM when the antisense oligonucleotide is transfected by electroporation.

EXAMPLE 2

Real-time Quantitative PCR Analysis of TARC mRNA Levels

Quantitation of TARC mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µof RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

Gene target-specific primers and probes for use in real-time PCR

| Species | Target SEQ ID NO | Sequence Description | Sequence (5' to 3') | SEQ ID NO |
|---|---|---|---|---|
| Human | 1 | Fwd Primer | CAAAGCCTTGAGAGGTCTTGAAG | 4 |
| Human | 1 | Rev Primer | CGGTGGAGGTCCCAGGTAGT | 5 |
| Human | 1 | Probe | TCCTCACCCCAGACTCCTGACTG | 6 |
| Mouse | 3 | Fwd Primer | GTTCCAGGGATGCCATCGT | 7 |
| Mouse | 3 | Rev Primer | CCTTCTTCACATGTTTGTCTTTGG | 8 |
| Mouse | 3 | Probe | TCTGACTGTCCAGGGCAAGCTCATCTG | 9 |

EXAMPLE 3

Antisense Inhibition of Human TARC Expression by Antisense Compounds

A series of antisense compounds was designed to target different regions of human TARC RNA, using published sequences or portions of published sequences as cited in Table 1. Methods for designing and testing antisense oligonucleotides for inhibition of mRNA target expression are discussed herein and well known to those skilled in the art. The screen identified active target segments within the human TARC mRNA sequence, specifically GenBank number NM_002987.2 (SEQ ID NO: 1). Each active target segment was targeted by multiple, active antisense oligonucleotides were targeted. These regions include nucleotides 60 to 172, including the subset of 60 to 100, and nucleotides 574 to 605 of SEQ ID NO: 1. Each of the oligonucleotides tested within each of these regions inhibited expression of human TARC at least 25%. Over half of the oligonucleotides tested inhibited expression at least 40%. In a preferred embodiment, antisense compounds have target sites of nucleotide 66, 77, 574, 591, and 596. The target site indicates the 5'-most nucleotide number on the particular target sequence to which the antisense compound binds. The screen also identified inactive target segments, regions to which multiple inactive antisense oligonucleotides were targeted. These regions include nucleotides 1-29 of SEQ ID NO: 1. Identification of these regions allows for the design of antisense oligonucleotides that modulate the expression of TARC.

EXAMPLE 4

Dose Dependent Reduction of TARC RNA Expression in 3T3-L1 Cells

A series of antisense compounds was designed to target different regions of mouse TARC RNA, using published sequences cited in Table 1. From this screen, two of the oligonucleotides found to be active were selected for further analysis, ISIS 220044 (nt 577 to 596 of SEQ ID NO: 3) and ISIS 220045 (nt 580 to 599 of SEQ ID NO: 3). Undifferentiated 3T3-L1 cells were plated at 4000 cells per well in 96 well plates with 100 ul DMEM (high glucose) and 10% FBS. Cells were treated with ISIS 220044, ISIS 220045, or a non-specific oligonucleotide, using LIPOFECTIN™. Total RNA was purified using the RNAeasy 96 plate kit. RNA levels were quantitated by RT-PCR using methods described above. ISIS 220044 and 220045 are chimeric oligonucleotides ("gapmers") 20 nucleotides in length, composed of a central "gap" region consisting of 10 2'-deoxynucleotides, which is flanked on both sides (5' and 3') by five-nucleotide "wings." The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines.

Both of the TARC specific ASOs gave a dose dependent reduction in the target RNA. No significant change in RNA levels were observed with a control, non-specific ASO. This demonstrates that the TARC ASOs are working via a target specific mechanism.

EXAMPLE 5

Mouse Models of Allergic Inflammation

Figure 1:
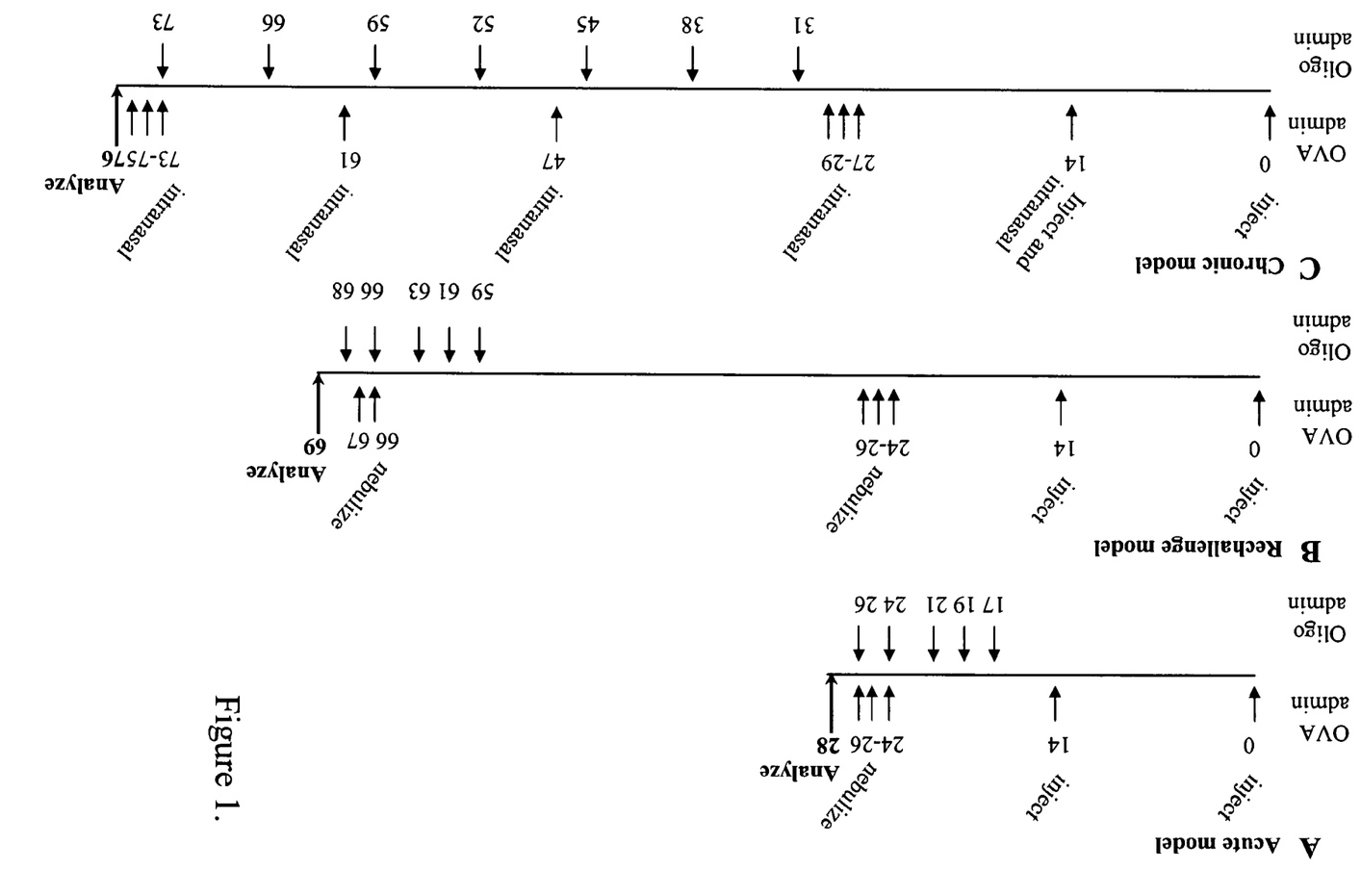
FIG. 1 shows multiple animal models have been designed to reflect various aspects of asthma.

Asthma is a complex disease with variations on disease severity and duration. In view of this, multiple animal models have been designed to reflect various aspects of the disease (see FIG. 1). It is understood that the models have some flexibility in regard to days of sensitization and treatment, and that the timelines provided reflect the days used herein. There are several important features common to human asthma and the mouse model of allergic inflammation. One of these is pulmonary inflammation, in which production of Th2 cytokines, e.g., IL 4, IL 5, IL 9, and IL 13 is dominant. Another is goblet cell metaplasia with increased mucus production. Lastly, airway hyperresponsiveness (AHR) occurs, resulting in increased sensitivity to cholinergic receptor agonists such as acetylcholine or methacholine.

Ovalbumin Induced Allergic Inflammation—Acute Model

The acute model of induced allergic inflammation is a prophylaxis treatment paradigm. Animals are sensitized to allergen by systemic administration (i.e., intraperitoneal injection), and treated with the therapeutic agent prior to administration of the pulmonary allergen challenge (see FIG. 1A). In this model, there is essentially no pulmonary inflammation prior to administration of the therapeutic agent.

Balb/c mice (Charles River Laboratory, Taconic Farms, N.Y.) were maintained in micro-isolator cages housed in a specific pathogen free (SPF) facility. The sentinel cages within the animal colony surveyed negative for viral antibodies and the presence of known mouse pathogens. Mice were sensitized and challenged with aerosolized chicken OVA. Briefly, 20 ug of alum precipitated OVA was injected intraperitoneally on days 0 and 14. On days 24, 25 and 26, the animals were exposed for 20 minutes to 1% OVA (in saline) by ultrasonic nebulization using a Lovelace nebulizer (Model 01-100). On days 17, 19, 21, 24, and 26 animals were dosed intratracheally with 0.01 ug/kg, 0.1 ug/kg, or 1 ug/kg of ISIS 220044, ISIS 220045, or vehicle control (0.9% normal saline). Analysis was performed on day 28.

Delivery of Antisense Oligonucleotides to the Lung by Intratracheal Instillation A study was performed to determine if intratracheal administration could be used to effectively deliver oligonucleotides throughout the lung. Distribution of an ASO that can be detected by direct immunohistochemical staining (ISIS 13920, 5'-TCCGTCATCGCTCCTCAGGG-3', SEQ ID NO: 10) was assayed by staining of thin lung sections. The ASO was delivered predominantly to alveolar macrophages and epithelium in the lung. This demonstrates that intratracheal administration can be used for the delivery of therapeutic agents to the lung.

Effect of IT Administered ASOs Targeted to TARC on Airway Hyperreponsiveness in Response to Methacholine Airway responsiveness was assessed by inducing airflow obstruction with a methacholine aerosol using a noninvasive method. This method used unrestrained conscious mice that are placed into a test chamber of a plethsmograph (Buxco Electronics, Inc. Troy, N.Y.). Pressure difference between this chamber and a reference chamber were used extrapolate minute volume, breathing frequency and enhanced pause (Penh). Penh is a dimensionless parameter that is a function of total pulmonary airflow in mice (i.e. the sum of the airflow in the upper and lower respiratory tracts) during the respiratory cycle of the animal. A lower Penh is indicative of greater the airflow. This parameter is known to closely correlate with lung resistance as measured by traditional, invasive techniques using ventilated animals (see e.g., Hamelmann et al., 1997).

ISIS 220044 and 220045, but not the vehicle control oligonucleotide, caused a significant, dose dependent suppression in methacholine induced AHR in sensitized mice as measured by whole body plethysmography. The data are shown in Table 3.

Data are presented as group means, N=10/group. *$p<0.05$ vs. vehicle treated controls by Students's T-test.

TABLE 3

Measurement of AHR by Penh in Response to Methacholine in Acute Allergen-challenged Mice

| Treatments | | Baseline | Methacholine dose (mg/kg) | | | | | | |
|---|---|---|---|---|---|---|---|---|---|
| | | | 0 | 3 | 6 | 12 | 25 | 50 | 100 |
| 220044 | 0.01 ug/kg | 0.42 | 0.38 | 0.64 | 1.03 | 1.32 | 1.88 | 2.59* | 4.00* |
| 220044 | 0.1 ug/kg | 0.44 | 0.42 | 0.78 | 1.31 | 1.66 | 1.89 | 2.88* | 3.18* |
| 220044 | 1.0 ug/kg | 0.45 | 0.41 | 0.67 | 1.23 | 2.32 | 3.36 | 4.29 | 5.05* |
| 220045 | 0.01 ug/kg | 0.45 | 0.41 | 0.74 | 1.18 | 1.47 | 1.92 | 2.77* | 3.61* |
| 220045 | 0.1 ug/kg | 0.47 | 0.41 | 0.83 | 1.18 | 1.56 | 2.22 | 2.65* | 3.47* |
| 220045 | 1.0 ug/kg | 0.48 | 0.40 | 0.78 | 1.26 | 1.74 | 2.10 | 2.95* | 3.94* |
| Vehicle | | 0.44 | 0.38 | 0.86 | 1.27 | 1.66 | 2.79 | 5.14 | 5.67* |
| Naïve | | 0.46 | 0.42 | 0.60 | 0.96 | 1.43 | 1.72 | 1.96* | 2.15* |

These data confirm that oligonucleotides targeted to TARC are effective in the treatment of AHR in a prophylaxis paradigm. The results were confirmed for ISIS 220045 in a separate mismatch oligonucleotide control study. A significant (p<0.05 v. control) decrease in Penh in response to 100 mg/kg methocholine was seen in both dosage groups (0.01, 0.1 and 1.0 mg/kg).

Effect of IT Administered ASOs Targeted to TARC on Inflammatory Cell Infiltration The effect of ISIS 220044 and 220045 on inflammatory cell profiles was analyzed (Mac=macrophage; Lym=lymphocyte; Eos=eosinophil; and Neu=neutrophil). Cell differentials were performed on bronchial alveolar lavage (BAL) fluid collected from lungs of the treated mice after injection of a lethal dose of ketamine. Treatment with ISIS 220044 and 220045, but not the vehicle control, resulted in a significant decrease in BAL eosinophil (eos) infiltration. The data are shown in Table 4.

Data are presented as group means, N=8/group, of percent inflammatory cell type. *p<0.05 vs. vehicle treated controls by Student's T-test.

TABLE 4

Measurement of Airway Inflammatory Cells in Acute Allergen-challenged Mice

| Treatment | | Mac | Lym | Eos | Neu |
|---|---|---|---|---|---|
| 220044 | 0.01 ug/kg | 93.8 | 3.2 | 3.5* | 0 |
| 220044 | 0.1 ug/kg | 94.4 | 2.0 | 3.2* | 0.4 |
| 220044 | 1.0 ug/kg | 86.2 | 3.3 | 8.3* | 2 |
| 220045 | 0.01 ug/kg | 93.0 | 4.2 | 2.8* | 0 |
| 220045 | 0.1 ug/kg | 94.2 | 2.7 | 2.5* | 0.5 |
| 220045 | 1.0 ug/kg | 92.3 | 1.8 | 5.8* | 0 |
| Vehicle | | 51.7 | 6.2 | 41.0 | 1.2 |
| Naïve | | 92.7 | 1.0 | 1.7* | 4.7 |

These results demonstrate that an oligonucleotide targeted to TARC decreased pulmonary inflammation by decreasing eosinophil infiltration.

These data demonstrate that TARC is a valid target for the prevention of AHR and lung inflammation, and disease associated therewith.

TARC Expression in BAL

The effect of ISIS 220044 and 220045 on TARC expression levels in BAL fluid was assessed by ELISA using a commercially available kit (R&D Systems, Inc., Minneapolis, Minn.). A dose dependent trend in the expression of TARC production was seen in response to treatment with ISIS 220044. A trend towards decreased TARC expression was also observed with ISIS 220045, but the decrease was not dose dependent. (N=5)

Mucus Production

Mucus is an indicator of pulmonary inflammation. The effect of ISIS 220044 and 220045 on mucus cell development along the airway epithelium was assessed in paraffin embedded tissue sections (4 um) stained with periodic acid Schiff's reagent (PAS). Parasagittal tissue sections were analyzed by bright field microscopy, and images were collected. The total PAS-positive airways in a lung section were counted.

Treatment with ISIS 20044 and 220045 reduced mucus production in the lung at all doses of the ASOs (*p<0.05 vs vehicle control group by paired Student's T-test, N=6/group). Data are presented as group means in Table 5.

TABLE 5

Measurement of PAS-positive Airways in Acute Allergen-challenged Mice

| Treatment | | Percent PAS-positve airways |
|---|---|---|
| 220044 | 0.01 ug/kg | 17.8* |
| 220044 | 0.1 ug/kg | 24.2* |
| 220044 | 1.0 ug/kg | 23.0* |
| 220045 | 0.01 ug/kg | 20.2* |
| 220045 | 0.1 ug/kg | 16.5* |
| 220045 | 1.0 ug/kg | 20.0* |
| Vehicle | | 39.5 |
| Naïve | | 0.2* |

The results demonstrate that an oligonucleotide targeted to TARC decreased pulmonary inflammation in a prophylaxis treatment paradigm by decreasing mucus production.

These data demonstrate that TARC targeted antisense oligonucleotide approach is efficacious in decreasing pulmonary inflammation and airway hyperresponsiveness, and that TARC is an appropriate target for the amelioration, and/or treatment of AHR and pulmonary inflammation, and diseases assosiated therewith.

Mouse Model of Allergic Inflammation—Rechallenge Model

The rechallenge model of induced allergic inflammation allows testing of a pharmacologic approach in mice that have been previously sensitized and then exposed to an aeroallergen. During the first set of local allergen challenges, the mice develop allergen-specific memory T lymphocytes. Subsequent exposure to a second set of inhaled allergen challenges produces an enhanced inflammatory response in the lung, as demonstrated by increased levels of Th2 cytokines in lavage fluid. The rechallenge model of allergic inflammation includes a second series of aerosolized administration of OVA on days 59 and 60 in addition to the two IP OVA administrations on days 0 and 14 and the nebulized OVA administration of days 24, 25 and 26 of the acute model (see FIG. 1B). Using this model, oligonucleotide treatment occurs after the first set of local allergen challenges. This also allows for the evaluation of the target's role in a recall response, as opposed to an initial immune response.

In the rechallenge model, mice are treated with about 0.1 ug/kg to about 500 ug/kg of at least one oligonucleotide targeted to TARC; and a mismatch control oligonucleotide and/or a vehicle control (i.e., 0.9% normal saline) on days 59, 61, 63, 66, and 68 delivered by nose only inhalation. Oligonucleotides are suspended in 0.9% sodium chloride and delivered via inhalation using a nose-only exposure system. A Lovelace nebulizer (Model 01-100) is used to deliver the oligonucleotide into an air flow rate of 1.0 liter per minute feeding into a total flow rate of 10 liters per minute. The exposure chamber is equilibrated with an oligonucleotide aerosol solution for 5 minutes before mice are placed in a restraint tubes attached to the chamber. Restrained mice are treated for a total of 10 minutes. The study endpoints include many of those used in the acute model: Penh response (i.e., AHR reduction), inflammatory cells in BAL, mucus accumulation, cytokine production, and lung histology. TARC protein reduction in pulmonary structural and inflammatory cells can also be evaluated. Methods to evaluate these endpoints are discussed herein and are well known to those skilled in the art.

Mouse Model of Allergic Inflammation—Chronic Model

The chronic model of induced allergic inflammation uses a therapeutic treatment regimen, with ASO treatment initiated after the establishment local pulmonary inflammation. The chronic model recapitulates some of the histological features of severe asthma in humans, including collagen deposition and lung tissue remodeling. The chronic OVA model produces a more severe disease than that observed in the acute or rechallenged model.

This model includes intranasal OVA administration on days 14, 27-29, 47, 61, and 73-75, at a higher dose (500 ug) than in the acute and chronic models, in addition to the two OVA IP administrations on days 0 and 14 (see FIG. 1C). Intranasal administration of the allergen results in a higher dose of the allergen delivered to the lungs relative to delivery by nebulizer. The increased number of allergen challenges produces more severe inflammatory events, resulting in increased lung damage and pathology more reflective of clinical asthma than other models, in the absence of therapeutic interventions.

Endpoints tested are similar to those in the acute and rechallenge model, including Penh (AHR), BAL inflammatory cells and cytokines, lung histology, and mucus accumulation. This model also allows for the analysis of endpoints typically associated with chronic diseases, such as asthma and COPD, including subepithelial fibrosis, collagen deposition, enhanced goblet cell metaplasia, and smooth muscle cell hyperplasia.

Oligonucleotide and control solutions are administered by nose-only aerosol at a dose of from about 0.1 mg/kg to about 500 ug/kg on or around days 31, 38, 45, 52, 59, 66 and 73. Analysis of endpoints is performed on or around day 76, except cytokines which are evaluated on or around day 62, typically about 6 hours post OVA challenge.

EXAMPLE 6

Mouse Model of Allergic Inflammation, Analysis for Nasal Rhinitis Endpoints

Mouse models of allergen—induced acute and chronic nasal inflammation similar to the allergic inflammation models above have been used to study allergic rhinitis in mice (Hussain et al., Larangyoscope. 112: 1819-1826. 2002; Iwasaki et al., J. Allergy Clin Immunol. 112: 134-140. 2003; Malm-Erjefaelt et al., Am J Respir Cell Mol Biol. 24:352-352.2001; McCusker et al., J Allergy Clin Immunol., 110: 891-898; Saito et el., Immunology. 104:226-234. 2001). In all of the models, the mice are sensitized to OVA by injection, as above, followed by intranasal OVA instillation.

The most substantial difference in the models is in the endpoints analyzed. Endpoints include, but are not limited to, the amount of sneezing and nasal scratching immediately after administration of allergen challenge (i.e. intranasal OVA), and nasal histology including mucus and eosinophil counts and measurements of cytokines or other inflammatory products in nasal lavage fluid or nasal tissues. Methods for performing such analyses are detailed in the references cited which are incorporated herein by reference.

What is claimed is:

1. A compound comprising a modified oligonucleotide consisting of 12 to 35 linked nucleosides and having a nucleobase sequence comprising at least 8 contiguous nucleobases fully complementary to an equal length portion of nucleobases 60 to 172 of SEQ ID NO: 1, wherein the nucleobase sequence of the modified oligonucleotide is at least 95% complementary to SEQ ID NO: 1 over the entire length of the oligonucleotide, and wherein said modified oligonucleotide has at least one modified internucleoside linkage, modified sugar moiety, or modified nucleobase.

2. The compound of claim 1, wherein the modified oligonucleotide is 100% complementary to SEQ ID NO: 1 over the entire length of the oligonucleotide.

3. The compound of claim 1, wherein the modified oligonucleotide hybridizes exclusively within nucleobases 60 to 172 of SEQ ID NO: 1.

4. The compound of claim 3, wherein the modified oligonucleotide hybridizes exclusively within nucleobases 60 to 100 of SEQ ID NO: 1.

5. The compound of claim 2, wherein the modified oligonucleotide hybridizes exclusively within nucleobases 60 to 172 of SEQ ID NO: 1.

6. The compound of claim 5, wherein the modified oligonucleotide hybridizes exclusively within nucleobases 60 to 100 of SEQ ID NO: 1.

7. The compound of claim 1, consisting of a single-stranded modified oligonucleotide.

8. The compound of claim 7, wherein each internucleoside linkage is a phosphorothioate internucleoside linkage.

9. The compound of claim 7, wherein the modified oligonucleotide comprises at least one modified sugar that is a bicyclic sugar.

10. The compound of claim 7, wherein the modified oligonucleotide comprises at least one modified sugar that is a 2'-O-methoxyethyl.

11. The compound of claim 7, wherein the modified oligonucleotide comprises at least one modified nucleobase that is a 5-methylcytosine.

12. The compound of claim 1, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

13. The compound of claim 12, wherein the modified oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

14. The compound of claim 7, wherein the modified oligonucleotide consists of 20 linked nucleosides.

15. A composition comprising the compound of claim 1 or a pharmaceutically acceptable salt thereof, and a pharmaceutically acceptable penetration enhancer, carrier, or diluent.

16. The composition of claim 15, consisting of a single-stranded oligonucleotide.

17. The composition of claim 15, wherein the modified oligonucleotide consists of 20 linked nucleosides.

18. A compound comprising a modified oligonucleotide consisting of 15 to 35 linked nucleosides and having a nucleobase sequence comprising at least 12 contiguous nucleobases fully complementary to an equal length portion of nucleobases 60 to 172 of SEQ ID NO: 1, wherein the nucleobase sequence of the modified oligonucleotide is at least 95% complementary to SEQ ID NO: 1 over the entire length of the oligonucleotide, and wherein said modified oligonucleotide has at least one modified internucleoside linkage, modified sugar moiety, or modified nucleobase.

19. The compound of claim 18, consisting of a single-stranded modified oligonucleotide.

20. The compound of claim 19, wherein the nucleobase sequence of the modified oligonucleotide is 100% complementary to SEQ ID NO: 1 over the entire length of the oligonucleotide.

21. The compound of claim 19, wherein each internucleoside linkage is a phosphorothioate internucleoside linkage.

22. The compound of claim 19, wherein the modified oligonucleotide comprises at least one modified sugar that is a bicyclic sugar.

23. The compound of claim 19, wherein the modified oligonucleotide comprises at least one modified sugar that is a 2'-O-methoxyethyl.

24. The compound of claim 19, wherein the modified oligonucleotide comprises at least one modified nucleobase that is a 5-methylcytosine.

25. The compound of claim 18, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

26. The compound of claim 25, wherein the modified oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

27. The compound of claim 19, wherein the modified oligonucleotide consists of 20 linked nucleosides.

28. A composition comprising the compound of claim 18 or a pharmaceutically acceptable salt thereof, and a pharmaceutically acceptable penetration enhancer, carrier, or diluent.

29. The composition of claim 28, consisting of a single-stranded oligonucleotide.

30. The composition of claim 28, wherein the modified oligonucleotide consists of 20 linked nucleosides.

* * * * *

SEQUENCE LISTING

```
<160> NUMBER OF SEQ ID NOS: 10

<210> SEQ ID NO 1
<211> LENGTH: 615
<212> TYPE: DNA
<213> ORGANISM: Homo sapiens

<400> SEQUENCE: 1
gctcagagag aagtgacttt gagctcacag tgtcaccgcc tgctgatggg agagctgaat      60
tcaaaaccag ggtgtctccc tgagcagagg gacctgcaca cagagactcc ctcctgggct     120
cctggcacca tggccccact gaagatgctg gccctggtca ccctcctcct gggggcttct     180
ctgcagcaca tccacgcagc tcgagggacc aatgtgggcc gggagtgctg cctggagtac    240
ttcaagggag ccattcccct tagaaagctg aagacgtggt accagacatc tgaggactgc    300
```

| | |
|---|---|
| tccagggatg ccatcgtttt tgtaactgtg cagggcaggg ccatctgttc ggaccccaac | 360 |
| aacaagagag tgaagaatgc agttaaatac ctgcaaagcc ttgagaggtc ttgaagcctc | 420 |
| ctcaccccag actcctgact gtctcccggg actacctggg acctccaccg ttggtgttca | 480 |
| ccgcccccac cctgagcgcc tgggtccagg ggaggccttc cagggacgaa gaagagccac | 540 |
| agtgagggag atcccatccc cttgtctgaa ctggagccat gggcacaaag gcccagatt | 600 |
| aaagtcttta tcctc | 615 |

<210> SEQ ID NO 2
<220> FEATURE:

<400> SEQUENCE: 2

000

<210> SEQ ID NO 3
<211> LENGTH: 602
<212> TYPE: DNA
<213> ORGANISM: Mus musculus

<400> SEQUENCE: 3

| | |
|---|---|
| gggtacagtg aaaaacccaa ggccatgaca agggtacggc tgcgagaaga cgacagaagg | 60 |
| gtacggctgc gagaagacga cagaaggggga agacaggcag aaggacccat gaagaccttc | 120 |
| acctcagctt ttggtaccat gaggtcactt cagatgctgc tcctggctgc tctgcttctg | 180 |
| gggactttc tgcagcatgc cagagctgct cgagccacca atgtaggccg agagtgctgc | 240 |
| ctggattact tcaaggggc cattcctatc aggaagttgg tgagctggta taagacctca | 300 |
| gtggagtgtt ccagggatgc catcgtgttt ctgactgtcc agggcaagct catctgtgca | 360 |
| gaccccaaag acaaacatgt gaagaaggcc atcagattgg tgaaaaaccc aaggccatga | 420 |
| ccttcccgct gaggcatttg gagacgccag ggctgctgtc catggtttca acataaaacg | 480 |
| gcctgtgacc agcagagccc aagagcagcc atcgagcaga agtccctgtt cccttttta | 540 |
| tggactctta tgcactacag gcgaacacaa aaaaagcaa cggaataaag ccttcctccc | 600 |
| tc | 602 |

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4

| | |
|---|---|
| caaagccttg agaggtcttg aag | 23 |

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

| | |
|---|---|
| cggtggaggt cccaggtagt | 20 |

<210> SEQ ID NO 6
<211> LENGTH: 23
<212> TYPE: DNA
<213> ORGANISM: Artificial Sequence

```
<220> FEATURE:
<223> OTHER INFORMATION: Probe

<400> SEQUENCE: 6
tcctcacccc agactcctga ctg                                          23

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gttccaggga tgccatcgt                                               19

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ccttcttcac atgtttgtct ttgg                                         24

<210> SEQ ID NO 9
<211> LENGTH: 27
<212> TYPE: DNA
<213> ORGANISM: Artificial Sequence
<220> FEATURE:
<223> OTHER INFORMATION: Probe

<400> SEQUENCE: 9
tctgactgtc cagggcaagc tcatctg                                      27

<210> SEQ ID NO 10
<211> LENGTH: 20
<212> TYPE: DNA
<213> ORGANISM: Artificial Sequence
<220> FEATURE:
<223> OTHER INFORMATION: Antisense Compound

<400> SEQUENCE: 10
tccgtcatcg ctcctcaggg                                              20
```